United States Patent [19]
Fratamico et al.

[11] Patent Number: 5,652,102
[45] Date of Patent: Jul. 29, 1997

[54] ASSAY FOR ENTEROHEMORRHAGIC ESCHERICHIA COLI 0157:H7 BY THE POLYMERASE CHAIN REACTION

[75] Inventors: Pina M. Fratamico, Elkins Park; Solomon K. Sackitey, Norristown, both of Pa.; Martin Wiedmann, Ithaca, N.Y.

[73] Assignee: The United States of America as represented by the Secretary of Agriculture, Washington, D.C.

[21] Appl. No.: 357,791

[22] Filed: Dec. 5, 1994

[51] Int. Cl.[6] .................. C07H 21/02; C07H 21/04; C12P 19/34; C12Q 1/68
[52] U.S. Cl. ............... 435/6; 435/91.1; 435/91.2; 536/23.7; 536/24.32; 536/24.33
[58] Field of Search ............... 435/6, 91.1, 91.2; 536/24.33, 23.7, 24.32

[56] References Cited

U.S. PATENT DOCUMENTS

| | | | |
|---|---|---|---|
| 4,683,202 | 7/1987 | Mullis et al. | 435/91 |
| 5,189,151 | 2/1993 | Baudry et al. | 536/24.32 |
| 5,298,392 | 3/1994 | Atlas et al. | 435/600 |

OTHER PUBLICATIONS

Fratamico et al. J. Med. Microbiol. 39:371–381, 1993.
Brian et al. J. Clin. Microbiol. 30(7):1801–1806, 1992.
Yu et al. Mol. Microbiol. 6(3):411–417, 1992.
Jackson M.P. Mol. Cellular Probes 6:209–214, 1992.
Schmidt et al. Med. Microbiol. Immunol. 183:23–31, 1994.
Lang et al. Applied and Environm. Microbiol. 60(9):3145–3149, 1994.
Sequence Beares Printout, 1995, pp. 1–7.
Begum et al., J. of Clin. Microb., vol. 31(12), pp. 3153–3156 (Dec. 1993).
Gannon et al., Applied and Environ. Microb., vol. 58(12), pp. 3809–3815 (Dec. 1992).
Gannon et al., J. of Clin. Microb., vol. 31(5), pp. 1268–1274 (May 1993).
Karch and Meyer, J. of Clin. Microb., vol. 27(12), pp. 2751–2757 (Dec. 1989).

Primary Examiner—Stephanie W. Zitomer
Assistant Examiner—Paul B. Tran
Attorney, Agent, or Firm—M. Howard Silverstein; John Fado; Janelle S. Graeter

[57] ABSTRACT

Primers specific for enterohemorrhagic Escherichia coli (EHEC) 0157:H7 bacteria have been designed which are useful for detecting the bacteria by polymerase chain reaction methods. The primers were derived from DNA sequences contained within a 60-MDa plasmid which is present in most EHEC. The primers may also be used in combination with primers derived from other sequences of significance, the conserved sequences of Shiga-like toxins I and II and the eaeA gene, in a single simultaneous amplification reaction to specifically identify EHEC serotype 0157.

5 Claims, 2 Drawing Sheets

ASSAY FOR ENTEROHEMORRHAGIC ESCHERICHIA COLI O157:H7 BY THE POLYMERASE CHAIN REACTION

BACKGROUND OF THE INVENTION

1. Field of the Invention

Escherichia coli O157:H7, also known as enterohemorrhagic E. coli (EHEC), has been associated with recent outbreaks of foodborne diseases. Sporadic cases of hemorrhagic colitis and hemolytic uremic syndrome have occurred worldwide. These outbreaks have been attributed to the presence of the pathogenic microorganism in ground beef since beef and dairy cattle are known to carry the organism in their intestinal tracts and carcasses are frequently contaminated during the slaughter process. The most visible outbreak in the United States occurred in the Western states and involved over 500 cases and several deaths of young children. Investigations by the Centers for Disease Control indicate that EHEC is the third most important cause of foodborne illness in the U.S., and the incidence of the disease is increasing. There is thus a strong incentive to develop a quick and sensitive assay method for the detection of the microorganism in beef products such as ground beef, on beef carcasses during inspection and in cattle fecal specimens. This invention relates to novel primers which can be used to detect pathogenic E. coli by specifically amplifying a fragment of a plasmid found in all strains tested by polymerase chain reaction (PCR).

2. Background of the Invention

EHEC has emerged as a foodborne pathogen of considerable public health importance. Present detection methodologies for this pathogen in foods, however, are either expensive, time-consuming cumbersome, have low specificity and sensitivity or require extensive training to perform. Since most methods require prior enrichment steps, the amount of time needed to obtain final confirmatory results is prolonged.

Virtually all EHEC harbor a large ~60-MDa plasmid (Fratamico et al. 1993. J. Med. Microbiol. vol. 39, pp. 371–381). It is currently unknown whether the presence of the plasmid plays a role in virulence. Known virulence factors include the production of one or more types of bacteriophage-encoded Shiga-like toxins, SLTs or verotoxins (Strockbine et al. 1986. Infect. Immun. vol. 53, pp. 135–140; Karmali, M. A. 1989. Clin. Microbiol. Rev. vol. 2, pp. 15–38), and the ability of the bacteria to intimately adhere to the intestinal mucosa by an attaching and effacing mechanism (Tzipori et al. 1989. Infect. Immun. vol. 57, pp. 1142–1150).

It has been suggested that the protein product of the EHEC eaeA gene may be necessary for attaching and effacing adhesion (Yu and Kaper. 1992. Mol. Microbiol. vol. 6, pp. 411–417). The gene has been cloned and sequenced and the product determined to be a 97-kDa outer membrane protein, called intimin$_{O157}$ (Louie et al. 1993. Infect. Immun. vol. 61, pp. 4085–4092). The genes encoding SLT-I and SLT-II have also been cloned and sequenced (Jackson et al. 1987. FEMS Microbiol. Lett. vol. 44, pp. 109–114), and immunological and DNA-based methods such as DNA hybridization have been developed for the detection of SLT-producing E. coli (Gannon et al. 1992. Appl. Environ. Microbiol. vol. 58, pp. 3809–3815; Paton et al. 1993. J. Clin. Microbiol. vol. 31, pp. 3063–3067; Begum et al. 1993. J. Clin. Microbiol. vol. 31, pp. 3153–3156; Hull et al. 1993. vol. 31, pp. 1167–1172), for EHEC having the eaeA gene (Gannon et al. 1993. J. Clin. Microbiol. vol. 31, pp. 1268–1274) and for the large 60-MDa plasmid (Levine et al. 1987. J. Infect. Dis. vol. 156, pp. 175–182). These methods suffer from the drawbacks mentioned above, however, and the search for an improved method has continued in an effort to provide a rapid and sensitive assay for the detection of the microorganism.

SUMMARY OF THE INVENTION

We have discovered oligonucleotide sequences which specifically amplify a DNA fragment of the plasmid found in all EHEC strains tested. In accordance with this discovery, it is an object of the invention to provide the novel oligonucleotides as primers for polymerase chain reaction (PCR) assays for the specific detection and identification of EHEC.

It is also an object of the invention to provide PCR assay methods utilizing the novel primers.

Other objects and advantages of the invention will become readily apparent from the following description.

BRIEF DESCRIPTION OF THE DRAWINGS

FIG. 1a: PCR amplification of 10-fold dilutions of E. coli O157:H7, lanes 1–11 at $1 \times 10^9$ cfu/ml–$1 \times 10^{-1}$ cfu/ml; lane 12, negative control ($H_2O$ instead of bacterial suspension). FIG. 1b) Southern blot of gel in FIG. 1a).

FIG. 1a: agarose (1.6%) gel followed by ethidium bromide staining. FIG. 2b) Southern blot of gel in FIG. 2a).

DETAILED DESCRIPTION OF THE INVENTION

A portion of an EcoRI-HindIII DNA fragment of the 60-MDa plasmid harbored by virtually all EHEC strains was sequenced, and 20-mer single-stranded primers were designed. Plasmid pCVD419 (PBR325 containing a 3.4-kb fragment of the 60-MDa plasmid, provided by James Nataro, Center for Vaccine Development, Baltimore, Md.; Levine et al., supra) was digested with HindIII, and the isolated 3.4-kb fragment was then digested with EcoRI, yielding fragments of approximately 1.4 and 1.9 kb in size. The 1.4-kb fragment was subcloned into M13 mp19 using the M13 cloning kit (Boehringer Mannheim Corporation, Indianapolis, Ind.) according to the manufacturer's instructions. A portion of the 1.4-kb fragment was then sequenced using the Sequenase® version 2.0 kit (United States Biochemical Corporation, Cleveland, Ohio).

PCR primers, designed from the 1.4-kb fragment, are 5'-ACGATGTGGTTTATTCTGGA-3' (SEQ ID NO: 1) and 5'- CTTCACGTCACCATACATAT-3' (SEQ ID NO: 2) and have been designated MFS1F and MFS1R, respectively. The primers have been used to generate a 166-bp amplification product.

To confirm the identity of the 166-bp PCR product, amplified DNA was analyzed. Following agarose gel electrophoresis, Southern blots were prepared using a 3' end-labeled (digoxigenin-11-ddUTP) oligonucleotide probe (Genius 5 kit, Boehringer Mannheim), 5'-CCG TATCTTATAATAAGACGGATGTTGG-3' (SEQ ID NO: 3), which is internal to the primer pairs on the plasmid DNA fragment. A 166-bp hybridization signal was visible with all of the strains in which the amplification product was detectable on agarose gels.

Figures 1A, 1B:
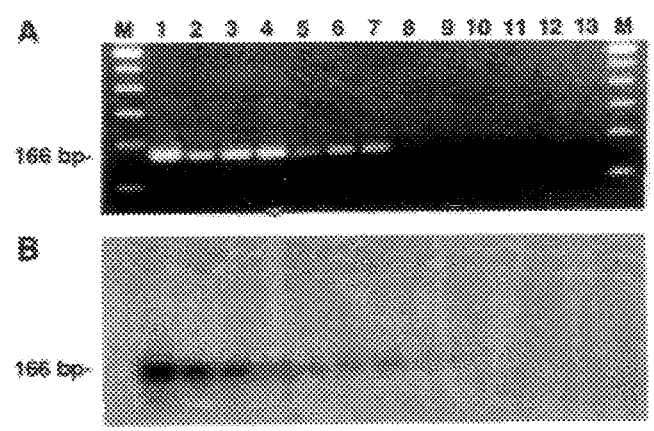
FIGS. 1a and 1b show the sensitivity of PCR for the detection of a 60-MDa plasmid of E. coli O157:H7 (EHEC)

To determine the sensitivity of the PCR, serial dilutions were prepared from a 4 h culture of EHEC strain B1409 grown in brain heart infusion broth (Difco). Following PCR amplification, the products were subjected to agarose (1.6%) gel electrophoresis. A 166-bp PCR product was generated with as little as 1.2 cfu (FIG. 1a). The PCR products were transferred to nylon membranes by Southern blotting (Sambrook et al. 1994. *Molecular cloning: a laboratory manual*, 2nd ed. Cold Spring Harbor Laboratory, Cold Spring Harbor, N.Y.) and hybridized with the internal probe 3' tailed with digoxigenin-11-dUTP/dATP prepared using the Genius 6 kit (Boehringer Mannheim) according to the manufacturer's instructions. Sensitivity of the PCR by colorimetric detection was 1.2–0.12 cfu (FIG. 1b).

The primers were tested with crude cell lysates from 148 bacterial strains (Table 1). PCR results of all of the *E. coli* 0157:H7, 0157:NM and 0157:H− strains tested showed a 166-bp amplification product on agarose gels. PCR of several other *E. coli* serotypes such as O26:H11 and O103:H2 also resulted in a 166-bp product. All the the non 0157 strains which were PCR-positive for the 60-MDa plasmid also possessed SLT DNA sequences.

Samples for the amplification process may be prepared by suspending a test sample in buffer and heating the suspension at a temperature and for a time sufficient to lyse the bacteria. For *E. coli*, heating at about 100° C for about 10 min is effective. Crude lysate is then added to reaction buffer comprising dNTPs, Taq DNA polymerase (Gibco/BRL, Gaithersburg, Md.) and the primers. Due to the sensitivity of the method, a preliminary step for culturing the samples in order to expand the number of microorganisms is generally unnecessary, thereby considerably reducing the amount of time required to process test samples. Preliminary concentration steps such as centrifugation and/or filtration may carried out, however, if desired.

Amplification is carried out according to conventional procedures well-known in the art (described by Mullis, U.S. Pat. No. 4,683,202, herein incorporated by reference). The amplified products may be visualized by ethidium bromide staining of

TABLE 1

PCR results of bacterial strains tested in this study

| bacterial strain | No. of strains | PCR using MFS1F and MFS1R plasmid | Multiplex PCR | | |
|---|---|---|---|---|---|
| | | | plasmid | SLTs | eaeA |
| *E. coli* | | | | | |
| 0157:H7 | 31 | 12/12 | 12/12 | 12/12 | 12/12 |
| 0157:H7 P−(a) | 3 | 0/4 | 0/4 | 4/4 | 4/4 |
| 0157:NM (SLT+) | 6 | 6/6 | 6/6 | 6/6 | 6/6 |
| 0157:NM (SLT−) | 1 | 0/1 | 0/1 | 0/1 | 0/1 |
| 0157:H | 1 | 1/1 | 1/1 | 1/1 | 1/1 |
| 026:H11 | 5 | 4/5 | 4/5 | 5/5 | 0/5 |
| 0111:NM | 4 | 1/4 | 1/4 | 1/4 | 0/4 |
| 0145:NM | 2 | 1/2 | 1/2 | 1/2 | 0/2 |
| 05:NM | 3 | 1/3 | 1/3 | 1/3 | 0/3 |
| 04:NM | 2 | 0/2 | 0/2 | 0/2 | 0/2 |
| 0125:NM | 1 | 0/1 | 0/1 | 1/1 | 0/1 |
| 0103:H2 | 3 | 3/3 | 3/3 | 3/3 | 0/3 |
| 045:H2 | 1 | 1/1 | 1/1 | 1/1 | 0/1 |
| 022:H8 | 1 | 1/1 | 1/1 | 1/1 | 0/1 |
| 091:H21 | 1 | 0/1 | 0/1 | 1/1 | 0/1 |
| 0113:H21 | 1 | 0/1 | 0/1 | 0/1 | 0/1 |
| 055:H7 | 3 | 0/3 | 0/3 | 1/3 | 3/3 |
| 078:K80:H12 | 1 | 0/1 | NT[b] | NT | NT |
| 029:NM | 1 | 0/1 | NT | NT | NT |
| K12 C600 | 1 | 0/1 | 0/1 | 0/1 | 0/1 |
| HB101 + pCVD419 | 1 | 1/1 | NT | NT | NT |
| HS | 1 | 0/1 | NT | NT | NT |
| JM109 | 1 | 0/1 | NT | NT | NT |
| JM103 | 1 | 0/1 | NT | NT | NT |
| V517 | 1 | 0/1 | NT | NT | NT |
| J53 (R16) | 1 | 0/1 | NT | NT | NT |
| ML35 | 1 | 0/1 | NT | NT | NT |
| B ATCC 11303 | 1 | 0/1 | NT | NT | NT |
| 078:H11 | 1 | 0/1 | 0/1 | 0/1 | 0/1 |
| 078:H12 | 1 | 0/1 | 0/1 | 0/1 | 0/1 |
| 025:NM | 1 | 0/1 | 0/1 | 0/1 | 0/1 |
| *Shewanella putrefaciens* | 1 | 0/1 | 0/1 | 0/1 | 0/1 |
| *Pseudomonas aeruginosa* | 5 | 0/5 | 0/1 | 0/1 | 0/1 |
| *Pseudomonas fluorescens* | 3 | 0/3 | 0/3 | 0/3 | 0/3 |
| *Shigella dysenteriae* | 1 | 0/1 | NT | NT | NT |
| *Shigella flexneri* | 2 | 0/2 | NT | NT | NT |
| *Shigella sonnei* | 1 | 0/1 | NT | NT | NT |
| *Salmonella typhimurium* | 5 | 0/5 | NT | NT | NT |
| *Salmonella enteriditis* | 4 | 0/4 | NT | NT | NT |
| *Salmonella arizonae* | 1 | 0/1 | NT | NT | NT |
| *Salmonella anatum* | 1 | 0/1 | NT | NT | NT |
| *Salmonella seftenberg* | 1 | 0/1 | NT | NT | NT |
| *Salmonella dublin* | 2 | 0/2 | NT | NT | NT |
| *Salmonella poona* | 1 | 0/1 | NT | NT | NT |
| *Aeromonas hydrophila* | 1 | 0/1 | NT | NT | NT |
| *Aeromonas pappu* | 1 | 0/1 | NT | NT | NT |
| *Staphylococcus aureus* | 4 | 0/4 | NT | NT | NT |
| *Vibrio parahemolyticus* | 1 | 0/1 | NT | NT | NT |
| *Yersinia enterocolitica* | 4 | 0/4 | NT | NT | NT |
| *Serratia marcescens* | 1 | 0/1 | NT | NT | NT |
| *Serratia liquefaciens* | 1 | 0/1 | NT | NT | NT |
| *Rhodococcus equis* | 1 | 0/1 | NT | NT | NT |
| *Listeria monocytogenes* | 18 | 0/18 | NT | NT | NT |
| *Listeria innocua* | 1 | 0/1 | NT | NT | NT |
| *Carnobacterium piscicola* | 1 | 0/1 | NT | NT | NT |
| *Streptococcus faecium* | 2 | 0/2 | NT | NT | NT |
| *Bacillus subtillis* | 2 | 0/2 | NT | NT | NT |
| *Bacillus cereus* | 1 | 0/1 | NT | NT | NT |
| *Bacillus thuringiensis* | 1 | 0/1 | NT | NT | NT |

(a) 60 MDa Plasmid-cured strains (4)
(b) NT, not tested by multiplex PCR agarose gels or by Southern or dot-blot hybridization techniques utilizing DNA sequences internal to the oligonucleotide primers. Effective amplification conditions are described in Example I.

The primers may also be used in combination with primers directed to other sequences of significance in a multiplex reaction, i.e. an amplification procedure where more than one set of primers amplifying more than one target DNA sequence are used simultaneously. Three sets of primers which have been found advantageous are those primers which amplify sequences of SLTs, the eaeA gene and the 60-MDa plasmid, already described. These primers have been reported to be highly specific for *E. coli* serogroup 0157. Primers used for amplification of conserved sequences of SLT-I and SLT-II are 5'-TTTACGATAGACTTCTCGAC-3' (SEQ ID NO: 4) AND 5'-CACATATAA ATTATTTCGCTC-3' (SEQ ID NO: 5) and have been designated MK1 and MK2, respectively (Karch and Meyer. 1989. *J. Clin. Microbiol.* vol. 27, pp. 2751–2757). They amplify fragments of 227- and 224-bp of the SLT-I and SLT-II genes, respectively. Primers used for amplification of the eaeA gene are 5'-CAGGTCGTCGTGTCTGCTAAA-3'

(SEQ ID NO: 6) and 5'-TCAGCGTGGTTGGATCAACCT-3' (SEQ ID NO: 7) and have been designated AE19 and AE20, respectively (Gannon et al., supra). They amplify a 1,087-bp fragment of the EHEC eaeA gene. An exemplary method of utilizing the three sets of primers is presented in Example II.

The specificity of the multiplex PCR for EHEC was evaluated with 62 bacterial strains comprising 16 E. coli 0157:H7, 8 E. coli 0157 (NM and H–), E. coli of other serotypes, Shewanella putrefaciens and Pseudomonas aeruginosa (Table 1). Amplification of the expected sizes for plasmid, SLT and eae genes were obtained with all E. coli of serotype 0157:H7, 0157:NM and 0157:H– except for one nontoxigenic 0157:NM strain which was negative for all three products. It is not surprising that there were no amplification products using the nontoxigenic 0157:NM strain since it has been reported that SLT-negative E. coli 0157 did not hybridize with gene probe CVD 419 (Levine et al., supra), and therefore did not possess the EHEC 60-MDa plasmid. Using a primer pair specific for the EHEC eae gene, they obtained an amplification product only with SLT-positive E. coli 0157. Toxigenic E. coli 0157:NM are frequently associated with cases of hemorrhagic colitis and hemolytic uremic syndrome (Bopp et al. 1987. J. Clin. Microbiol. vol. 25, pp. 1486–1489; Gunzer et al. 1992. J. Clin. Microbiol. vol. 25, pp. 1486–1489), therefore a method for specific detection of E. coli 0157:H7 and nonmotile toxigenic 0157 strains is extremely useful.

The 166-bp product obtained by amplification of the plasmid gene is generated with as little as 1.2 cfu. However, in the multiplex PCR, the detection limit of the eaeA gene product is about 100 cfu and of the SLT gene is about 1,000 cfu.

PCR results showed that all strains in which the plasmid sequence was amplified also possessed SLT sequences (Table 1). E. coli 091:H21, 0125:NM, one 026:H11 and one 055:H7 isolate possessed SLT sequences but were negative in the PCR using plasmid primers alone. Both plasmid sequence and SLT gene sequences were amplified in several E. coli serotypes including 0111:NM (1/4), 026:H11 (4/5), 0145:NM (1/2), 05:NM (1/3), 0103:H2 (3/3), 045:H2 (1/1) and 022:H8 (1/1). In none of these strains was the eaeA sequence amplified.

Multiplex PCR results showed an amplification product of the expected size (1,087 bp) with the 3 E. coli 055:H7 strains tested using primers AE19 and AE20 which are specific for the EHEC eaeA gene. These results are not surprising since it has been reported that by multilocus enzyme electrophoresis the 0157:H7 clone was most closely related to E. coli 055:H7 which has been recognized as a cause of diarrheal disease (Whittam et al. 1993. Infect. Immun. vol. 61, pp. 1619–1629). It was suggested that these two serotypes may have very similar eae genes since both form attaching and effacing lesions on intestinal epithelial cells. It has also recently been reported that serotypes 0157:H7 and 055:H7 strains have almost identical nucleotide and amino acid sequences in regions where the eaeA gene and protein product of enteropathogenic E. coli and EHEC differ (Louie et al. 1994. Epidemiol. Infect. vol. 112, pp. 449–461).

Figures 2A, 2B:
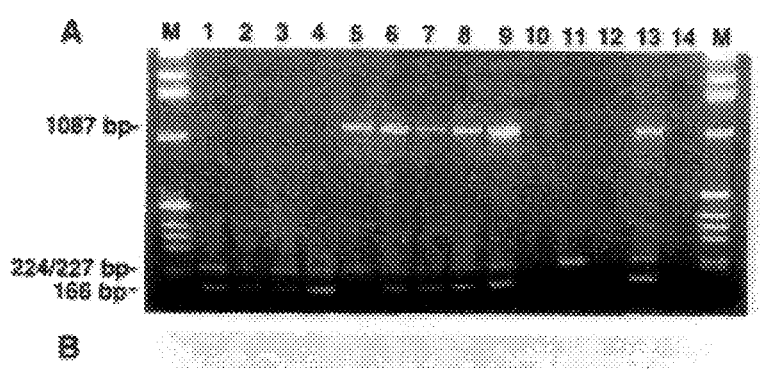
FIGS. 2a and 2b show the results of the multiplex PCR procedure using selected bacterial strains.

The amplified fragments obtained following multiplex PCR using several bacterial strains are shown in FIG. 2a. Following Southern blotting of the gel and hybridization with labeled internal probe (oligonucleotide internal to MFS1F and MFS1R primers 3' tailed with digoxigenin-11-dUTP/dATP), a hybridization signal was visible only in strains in which the 166-bp fragment was amplified (FIG. 2b). The probe did not hybridize with the SLT or eaeA products.

The value of screening clinical specimens or food samples for the presence of SLTs alone is questionable since other E. coli serotypes produce SLTs and many may not be clinically significant. Furthermore, it has been reported (Karch et al. 1992. Infect. Immun. vol. 60, pp. 3463–3467) that clinical E. coli isolates may lose SLT genes upon subcultivation. Screening for the EHEC eaeA gene may give rise to false-positive results as occurred with E. coli 055:H7 and, although virtually all EHEC 0157 strains possess the 60-MDa plasmid, several other toxigenic E. coli serotypes also harbor this plasmid. The multiplex PCR therefore should prove to be a very useful method for specific identification of EHEC 0157 since simultaneous detection of virulence genes (SLT and eaeA) and the 60-MDa plasmid is made possible. Additionally, using the multiplex PCR it is possible to determine whether the sample tested contains EHEC 0157 or other SLT-producing E. coli serotypes.

The following examples are intended only to further illustrate the invention and are not intended to limit the scope of the invention as defined by the claims.

EXAMPLES

Example I

Amplification of the 60-MDa Plasmid Fragment.

For PCR amplification of the plasmid fragment, a bacterial colony was transferred from nutrient agar (Difco Laboratories, Detroit, Mich.) to 200 µl of a solution consisting of 0.5% Triton X-100, 20 mM Tris, pH 8.0 and 2 mM EDTA, and the bacterial suspensions were heated at 100° C. for 10 min. The PCR reaction (total volume of 100 µl ) consisted of 5 to 10 µl of the crude cell lysate, 1.5 mM $MgCl_2$, 20 mM Tris (pH 8.0), 50 mM KCl, 0.001% gelatin, 200 µM (each) of dNTPs, 2.5 U of Taq DNA polymerase (Gibco/BRL, Gaithersburg, Md.) and 50 pmol of each primer. PCR reactions were performed in a thermal cycler (MJ Research, Inc., Watertown, Mass.) using the following cycling conditions: initial denaturation of 94° C. for 5 min and 94° C. for 30 sec, 55° C. for 30 sec and 72° C. for 90 sec for a total of 35 cycles. Following PCR amplification, the products were subjected to agarose (1.6%) gel electrophoresis followed by ethidium bromide staining.

Example II

Multiplex PCR.

The PCR reaction mixture was prepared as described in Example I with the exception that three sets of primers, MFS1F and MFS1R, MK1 and MK2, and AE19 and AE20 were added in equal concentrations. When the cycling conditions described in Example I were employed, however, only the plasmid and eaeA products were visualized by gel electrophoresis. Modifications in the cycling protocol were therefore made as follows: an initial denaturation at 94° C. for 5 min followed by 35 cycles of 94° C. for 1 min, 48° C. for 3 min and 72° C. for 4 min. Following PCR amplification, the products were subjected to agarose (1.6%) gel electrophoresis followed by ethidium bromide staining.

All references cited above are herein incorporated by reference.

We claim:

1. An oligonucleotide primer having the sequence 5'-ACGATGTGGTTTATTCTGGA-3' (SEQ ID NO: 1).

2. An oligonucleotide primer having the sequence 5'-CTTCACGTCACCATACATAT-3' (SEQ ID NO: 2).

3. A primer pair comprising two oligonucleotides one of which having the sequence 5'-ACGATGTGGTTTATTCTGGA-3' (SEQ ID NO: 1), the other having the sequence 5'-CTTCACGTCACCATACATAT-3' (SEQ ID NO: 2).

4. A method of detecting enterohemorrhagic *Escherichia coli* 0157:H7 bacteria by polymerase chain reaction, said method comprising a) providing a test sample suspected of containing the DNA of said bacterium,
  b) amplifying said DNA with a primer pair comprising two oligonucleotides one of which having the sequence 5'-ACGATGTGGTTTATTCTGGA-3' (SEQ ID NO: 1), and the other having the sequence 5'-CTTCACGTCACCATACATAT-3' (SEQ ID NO: 2),
  c) detecting the presence of amplified DNA as an indication of the presence of *Escherichia coli* 0157:H7.

5. The method of claim 4, wherein the amplifying step b) comprises two additional primer pairs having the sequences

| | |
|---|---|
| 5'-TTTACGATAGACTTCTCGAC-3' | (SEQ ID NO: 4), |
| 5'-CACATATAAATTATTTCGCTC-3' | (SEQ ID NO: 5), |
| 5'-CAGGTCGTCGTGTCTGCTAAA-3' | (SEQ ID NO: 6) | and

| | |
|---|---|
| 5'-TCAGCGTGGTTGGATCAACCT-3' | (SEQ ID NO: 7), | wherein SEQ ID NO: 4 and SEQ ID NO: 5 comprise one pair and SEQ ID NO: 6 and SEQ ID NO: 7 comprise another pair.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Escherichia coli
    ( B ) STRAIN: 0157:H7

( x i ) SEQUENCE DESCRIPTION: SEQ ID NO:1:

ACGATGTGGT TTATTCTGGA                                              20

( 2 ) INFORMATION FOR SEQ ID NO:2:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Escherichia coli
    ( B ) STRAIN: 0157:H7

( x i ) SEQUENCE DESCRIPTION: SEQ ID NO:2:

CTTCACGTCA CCATACATAT                                              20

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Escherichia coli
    ( B ) STRAIN: 0157:H7

( x i ) SEQUENCE DESCRIPTION: SEQ ID NO:3:

CTTCACGTCA CCATACATAT                                              20

( 2 ) INFORMATION FOR SEQ ID NO:4:

( i ) SEQUENCE CHARACTERISTICS:

(A) LENGTH: 20 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Escherichia coli
(B) STRAIN: 0157:H7

(xi) SEQUENCE DESCRIPTION: SEQ ID NO:4:

TTTACGATAG ACTTCTCGAC                    20

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Escherichia coli
(B) STRAIN: 0157:H7

(xi) SEQUENCE DESCRIPTION: SEQ ID NO:5:

CACATATAAA TTATTTCGCT C                   21

(2) INFORMATION FOR SEQ ID NO:6:

(i) SEQUENCE CHARACTERISTICS:
(A) LENGTH: 21 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Escherichia coli
(B) STRAIN: 0157:H7

(xi) SEQUENCE DESCRIPTION: SEQ ID NO:6:

CAGGTCGTCG TGTCTGCTAA A                   21

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
  (A) ORGANISM: Escherichia coli
  (B) STRAIN: 0157:H7

(xi) SEQUENCE DESCRIPTION: SEQ ID NO:7:

TCAGCGTGGT TGGATCAACC T                                                    21